United States Patent [19]
Chumakov et al.

[11] 4,004,974
[45] Jan. 25, 1977

[54] LIVE VIRUS CULTURE VACCINE AGAINST CARNIVORE DISTEMPER AND METHOD OF PRODUCING SAME

[76] Inventors: Mikhail Petrovich Chumakov, Leninsky prospekt 68/10, kv. 354; Inna Alexandrovna Prokhorova, Balaklavsky prospekt, 40, kv. 59, both of Moscow; Viktor Pavlovich Grachev, poselok Instituta poliomielita, 3, kv. 36, Moskovskaya oblast; Valentina Vasilievna Petukhova, proezd Dezhneva, 30, korpus 2, kv. 131, Moscow; Julia Anatolievna Svezhinina, poselok Instituta poliomielita, 2, kv. 34, Moskovskaya oblast; Ljubov Leonidovna Mironova, poselok Instituta poliomielita, 1, kv. 7, Moskovskaya oblast; Ninel Mikhailovna Ralf, poselok Instituta poliomielita, 3, kv. 33, Moskovskaya oblast; Valentina Dmitrievna Popova, bulvar Generala Karbysheva, 9, korpus 1, kv. 45, Moscow; Aida Nurislamovna Mustafina, poselok Instituta poliomielita, 4, kv. 127; Vladimir Ivanovich Chernyshev, poselok Instituta poliomielita, 3, kv. 4, both of Moskovskaya oblast, all of U.S.S.R.

[22] Filed: May 7, 1975

[21] Appl. No.: 575,220

[52] U.S. Cl. .................................. 195/1.3; 424/89
[51] Int. Cl.² .................... C12K 7/00; A61K 39/24
[58] Field of Search ....................... 195/1.3; 424/89

[56] References Cited

UNITED STATES PATENTS 3,836,626 9/1974 Lavender ........................... 195/1.3

*Primary Examiner*—Sam Rosen
*Attorney, Agent, or Firm*—Lackenbach, Lilling & Siegel

[57] ABSTRACT

A live virus culture vaccine against carnivore distemper.

Said vaccine is an attenuated strain of the carnivore distemper virus adapted to a cell culture of the kidney tissue of green monkeys and cultivated in said culture.

The method of producing said vaccine comprises infecting a cell culture of the kidney tissue of green monkeys with a carnivore distemper virus strain adapted to said culture and cultivating it in said culture.

The advantages offered by the proposed vaccine are standard properties, safety, adequate immunological activity and epizootological effectiveness as well as low production cost.

6 Claims, No Drawings

LIVE VIRUS CULTURE VACCINE AGAINST CARNIVORE DISTEMPER AND METHOD OF PRODUCING SAME

The present invention relates to industrial biology; more specifically, it is directed to a method of producing a live virus culture vaccine for immunization against carnivore distemper.

The prior art vaccines widely employed for immunization against carnivore distemper are likewise live virus culture vaccines prepared from chick-embryo or puppy-kidney tissue cultures.

Thus, the German vaccines "Candur B" and "Candur C" used for mink distemper prevention are prepared from a puppy-kidney tissue culture; the U.S. vaccine ASL and the Canadian vaccine "Connaught" are prepared from a chick-embryo tissue culture.

Said vaccines, though inducing an adequately high level of protection all have the following disadvantages: the vaccine prepared from the puppy-kidney tissue culture is liable to be contaminated with viruses pathogenic for fur bearers, e.g., hepatitis or rabies viruses; the vaccines prepared from the chick-embryo tissue culture are not standard enough. For both types of vaccines, each series usually includes virus yields from numerous stock cultures of said tissues, so that it is impossible to obtain high yields of an entirely homogeneous vaccine from a single culture (i.e. one produced from one embryo) with minimal spending on biological control of the suitability of each tissue culture source.

It is an object of the present invention to obviate the foregoing disadvantages.

Accordingly, the invention seeks to provide a novel method of producing an antidistemper vaccine whereby the tissue cultures of a single animal could yield large series of a highly standard, sufficiently immunogenic, safe and cheap vaccine.

It is an object of the present invention to provide an antidistemper vaccine which would be free from viruses pathogenic for the animals to be vaccinated.

It is another object of the present invention to provide a vaccine for carnivore distemper prevention which would be highly standard, sufficiently immunogenic, safe and cheap.

It is a further object of the invention to provide a method of producing an antidistemper vaccine exhibiting the above-described properties.

It is yet another object of the present invention to provide a method of producing said vaccine which would ensure a high yield of virus from the tissue cultures of a single animal.

It is still another object of the present invention to provide a method of producing said vaccine which would utilize widely available material.

These and other objects are attained in an antidistemper vaccine which, in accordance with the invention, is constituted by an attenuated strain of the carnivore distemper virus adapted to the culture of green monkey kidney cells and grown in said culture.

Said vaccine will be referred to hereinafter as "Vakchum" (a Russian abbreviation for antidistemper vaccine).

"Vakchum" offers the following advantages: it is adequately immunogenic, safe for the vaccinated animals regardless of their age, highly standard and free from contaminant-viruses pathogenic for carnivorous animals.

The proposed method of producing "Vakchum", in accordance with the invention, includes the steps of preadapting an attenuated strain of the carnivore distemper virus to the tissue culture of green monkey kidney cells, growing the thus adapted vaccine strain in the cell culture of green monkey kidney tissue in the presence of a suitable nutrient medium, removing from the resultant virus-containing fluid the degenerated cell detritus of said culture, and lyophilizing the liquid vaccine in the presence of a suitable virus thermostabilizer.

The term "cell culture of monkey-kidney tissue" implies the primary cell culture of monkey-kidney tissue the subculture and the continuous cell line. However, it might turn out more efficient to produce the proposed vaccine from the continuous cell lines of green monkey embryonal kidney.

The term "continuous cell lines" is to be construed as implying the cell cultures of green monkey embryonal kidney capable of unlimited growth, which may be cultivated in the course of an unlimited number of passages after being stored in liquid nitrogen.

Thanks to the above-described features of the continuous cell lines, "Vakchum" may be produced in any desired quantity no matter how many, if any, green monkeys are available.

However, the foregoing subculture of the green monkey kidney cells is also an effective feedstock for the production of the proposed vaccine, as subcultivation of the primary cells over 2 or 3 passages enables the yield of the cell mass, and consequently the yield of the vaccine, to be increased accordingly.

In accordance with the invention, use is made of an attenuated strain of the carnivore distemper virus which is preadapted to the cell culture of green monkey kidney tissue. The adaptation is carried out by several passages, e.g. 8 to 10 passages, at a temperature of from 33.8 to 34.2° C. until the incubation period of viral growth is cut back to 4 or 5 days.

Since the attenuated strain of the carnivore distemper virus is subjected to 8 to 10 passages in the green monkey kidney tissue culture, said strain becomes fully adapted to the cell culture (as confirmed by the shortening of the incubation period of virus development and by the rise in its titre), and the primary level of strain attenuation can be preserved. It is likewise possible to employ an attenuated strain adapted less stringently (4 or 5 passages), but in such a case the incubation period of virus development is lengthened by 5 to 10 days and its titres decrease by a substantial margin. The level of virus attenuation may be affected by varying the temperature of the procedure beyond the above-cited limits.

The virus adapted as shown hereinabove is used to prepare an inoculum from which the vaccine is produced.

The production of the vaccine is based on the inoculation principle.

The inoculum system provides for the preparation of a large amount of vaccine virus meeting all the requirements of the attenuated strain, i.e. it must withstand storage in liquid nitrogen and furnish material for the production of the vaccine as such need arises.

The proposed vaccine may be produced both from freshly trypsinized cell culture of green monkey kidney tissue and from one withdrawn from storage in liquid nitrogen.

The vaccine virus shall be grown in said cultures under rigorous temperature conditions (34.0 ± 0.2°

C.). In order to increase the virus yield and fully utilize the cell culture of said kidney tissue, it is recommended that the strain be grown in such a way that the virus-containing fluid is drained off and replaced by a fresh nutrient medium several times, the operation of virus-containing fluid replacement being effected for the first time when 30 to 400 percent of cells show a cytopathic effect (CPE); and this operation is repeated, i.e. the virus-containing fluid is drained off and a fresh nutrient medium placed instead, to the point of total cell degradation, usually 3 to 5 times.

The virus-containing fluid batches collected from the cell culture are pooled, freed from cell detritus by any known method, e.g. by settling followed by decantation, or using a separator, or else by low-speed centrifugal action.

To stabilize the virus, a suitable stabilizer is added to the product virus-containing fluid, e.g. 4.5 to 5.5 percent sorbite by weight and 1.4 to 1.6 percent gelatose by weight, after which the liquid is lyophilized.

At all the stages of "Vakchum" preparation sterile conditions are required.

The lyophilized preparation is subjected to biological tests on laboratory animals and in a culture tissue. The aim of these tests consists in determining the level of the vaccine virus in the preparation, sterility including control for the level of mycoplasm, safety and the level of contaminant-viruses pathogenic for carnivorous animals.

In case the test results are satisfactory, the preparation is regarded as a ready-for-use vaccine.

The invention offers several advantages over the prior art.

The proposed vaccine against carnivore distemper contains no viruses pathogenic for said animals as it is prepared in a green monkey kidney tissue culture heterogenous for carnivorous animals. Should said cultures happen to be contaminated with zoonotic viruses, the latter are readily identified by common biological control methods, and the affected cultures are discarded, whereas the prior art vaccines are susceptible to contamination with viruses which are pathogenic for carnivorous animals.

The high immunogenicity and low reactogenicity of the proposed vaccine are guaranteed by the adaptation conditions under which the strain retains all its attenuated properties, high immunological effectiveness and low reactogenicity.

The "Vakchum" preparation is highly standardized, which is achieved by the very high yield of the preparation in one series (from 100,000 to 2,000,000 vaccination doses), whereas the prior art vaccines are not standard enough, what with the small volume of the series.

The proposed vaccine contains a minimum of foreign proteins, ensuring the animals against allergic reactions; and the lack of contaminant-viruses pathogenic for carnivorous animals guarantees vaccine safety.

A further advantage of the present invention consists in the possibility of utilizing the cell cultures of green monkey kidney tissue which are discarded, for one reason or another, in the production of antipolio vaccines but which are suitable for "Vakchum" production. This feature favorably affects the economics of the process and permits cutting back heavily on the cost of the preparation, a substantial commercial advantage of "Vakchum" over the prior art antidistemper vaccines.

The method of producing "Vakchum" in accordance with the present invention lends itself to a far cheaper vaccine than all the prior art ones.

These and other advantages will become more apparent to those skilled in the art from the following detailed description of the invention.

The live culture virus vaccine against carnivore distemper in accordance with the invention is constituted by an attenuated strain of the carnivore distemper virus which is preadapted to the cell culture of green monkey kidney tissue and grown in said culture.

The antidistemper vaccine production is based on the inoculum system. The inoculum is an attenuated carnivore distemper virus, e.g. the strain isolated by Rokborn (Sweden). Such a virus is adapted to the cell culture of green monkey kidney tissue in the course of 8 to 10 passages at a temperature of 34.0° ± 0.2° C. Violation of said temperature conditions is undesirable for it may affect the properties of the attenuated virus.

In the course of adaptation, the incubation period of virus development is reduced and the first morphological alterations in the cells are observed 4 or 5 days after the inoculation together with a rise in the titre of the multiplied virus and an increase in the general yield of the vaccine virus in the cell culture grown in matrasses.

Adaptation of the attenuated strain to the cell culture of green monkey kidney tissue under the set of conditions specified hereinabove not only leads to a considerably higher virus yield but also ensures preservation of the strain attenuation level and its safety for the vaccinated animals, as well as its high immunological activity and epizootological efficiency.

The inoculum of the adapted strain is first subjected to all-round testing, including control tests for the presence of alien contaminant-viruses pathogenic for carnivorous animals, for microbial and mycoplasmatic sterility, for the virus titre, reactogenicity and immunological activity on susceptible animals (minks or polar foxes), after which it is dispensed into containers and lyophilized. The inoculum thus obtained and referred to as a primary inoculum is stored at a temperature of not higher than minus 20° C. A secondary inoculum is produced from the primary inoculum by one or two serial passages.

The secondary inoculum is grown in a cell culture of green monkey kidney tissue under the same conditions as these at which the primary inoculum is cultivated. The secondary inoculum is dispensed into flasks and stored in a frozen state at a temperature of not higher than minus 30° C. without prelyophilization. The secondary inoculum is tested for the presence of contaminant-viruses pathogenic for the carnivorous animals as well as for microbial and mycoplasmatic sterility and titre. After control tests show the absence of contaminant-viruses and an adequate level of microbial and mycoplasmatic sterility, the secondary inoculum is used to prepare a vaccine.

The carnivore distemper vaccine virus is grown by use of a freshly trypsinized cell culture of green monkey kidney tissue, subcultures, cell cultures or subcultures after storage in liquid nitrogen, and continuous cell lines of green monkey kidney tissue. It should be emphasized that the carnivore distemper vaccine virus can be grown in the cell cultures of green monkey kidney tissue discarded, for this or that reason, in the production of live antipolio vaccine but entirely suitable for the cultivation of the vaccine strain of the carnivore distemper virus as well as for the manufacture of a preventive preparation to control carnivore distemper.

The continuous cell lines of green monkey kidney tissue constitute the best material for producing the proposed antidistemper vaccine, because they enable the preparation to be produced independently of antipolio vaccine production and irrespective of whether or not the kidney tissue donors, i.e. green monkeys, are available. The continuous cell lines are capable of withstanding unlimited storage in liquid nitrogen; they can be used in any season and in any amount to produce an antidistemper vaccine. The above-listed cell cultures are cultivated in suitable media, such as 0.5% lactalbumin hydrolysate in Hanks' solution or Eagle's medium or a mixture of equal quantities of said media plus 5% of bovine serum.

Prior to infection of the cultures, the culture medium is removed from the culture glasses, the cultures are once rinsed with Earle's solution, and 3 to 6 ml of the secondary inoculum is introduced. After 1 hour's adsorption of the virus at a temperature between 33.8° and 34.2° C., 300 ml of a maintenance medium is placed in the culture glasses, the maintenance medium being composed of 0.5% lactalbumin hydrolysate in Earle's solution, pH 7.5, with 5% aminopeptide. As soon as the culture shows the first manifestation of virus multiplication, i.e. blurring of the cell picture and cell boundaries, the starting portion of the maintenance medium is removed to get rid of the interferon preventing further multiplication of the virus, and 500 ml of a fresh medium of the same composition is placed in the culture glasses instead. After 30 to 40 percent of all cells show degenerative alterations, the virus-containing medium is drained off and frozen, and the culture glasses are filled with the same amount of a fresh portion of the same medium. The next portion of the virus-containing fluid is harvested in 2 or 3 days' time depending on the dynamics of cytopathological changes in the cells. The virus-containing medium is repeatedly harvested and replaced by fresh portions thereof until all the cells are involved in cytopathological change. Usually it takes 3 to 5 harvests.

Each separate harvest of the virus-containing fluid is kept frozen at a temperature between −20 and −30° C. till the time of control tests for sterility and for the presence of contaminant-viruses pathogenic for the animals to be vaccinated. Following the control tests, provided the results are negative (the tests for the presence of foreign viruses are conducted on newborn and adult white mice, guinea pigs and rabbits), the separate batches of the virus-containing fluid are defrosted, poured into a single vessel, and the resultant pooled harvest is freed from the cell detritus, e.g. by centrifugal action.

To stabilize the virus in the detritus-free fluid, 4.5 to 5.5 percent sorbite by weight and 1.4 to 1.6 percent gelatose by weight are added. The mixture thus produced is thoroughly mixed, after which the preparation is ampuled and frozen at a temperature of minus 60° C.

After the freezing procedure, the vials are placed into a sublimator and lyophilized, the dried preparation having a residual moisture content of 3 to 5 percent.

The resultant preparation is tested for sterility, virus titre and safety on guinea pigs. Should the sterility and safety tests be negative and the virus titre results positive, the vaccine is regarded as a ready-for-use preparation that can be employed for preventive immunization of fur bearers and dogs. If bur-bearer immunization is to be effective, the mean vaccine dose must contain at least 1,000 plaque-forming units (PFU) of said strain. Usually, commercial vaccines contain no less than 3,000 plaque-forming units per dose. The lyophilized vaccine is effective for 1 year if it is stored at a temperature not higher than 4° C. If the preparation is stored at minus 20° C., the vaccine may retain its potency longer provided its virus content is at least 1,000 plaque-forming units, as determined by retitration.

The present invention will be further understood from the following examples, Examples 1 to 3 illustrating the proposed method of producing the "Vakchum" preparation and Examples 4 to 8 illistrating its practical application.

EXAMPLE 1

"Vakchum" manufacture by use of a primary cell culture of green monkey kidney tissue.

The cell culture was grown in 65 1.5-liter culture glasses in a nutrient medium composed of equal quantities of Hands' and Eagle's solutions with 0.5% lactalbumin hydrolysate, pH = 7.0, with 5% of normal bovine serum at a temperature of 37° C. After monolayer cultures were produced, the growth medium was removed and the cell cultures washed with Earle's solution, whereupon 5 ml of an inoculum comprising attenuated Rolborn's strain was introduced into each culture glass, the inoculum having been earlier passed 8 times in the cell cultures of green monkey kidney tissue at a temperature of 34° C. After 1 hour's adsorption of the virus at a temperature of 34° C., 300 ml of a nutrient medium comprising 0.5% lactalbumin hydrolysate in Earle's solution, pH = 7.5, with 5% aminopeptide was introduced into each culture. The infected cultures were incubated at a temperature of 34° C. The first manifestations of morphological changes in the cells testifying to virus multiplication were observed on the 5th day after the infection. The nutrient medium was thereupon removed and replaced by a 500 ml fresh portion of the same medium. The first harvesting of the virus and replacement of the nutrient medium of the foregoing composition were carried out on the 8th day; the second on the 11th day; the third on the 15th day; and the fourth, and last, on the 19th day. All in all, 115 liters of the virus-containing fluid were harvested; after the virus-containing fluid was freed from cell detritus, virus stabilizers (5% sorbite and 1 1.5% gelatose) were added thereto.

The virus-containing fluid was dispensed into 100-ml vials, 33 ml per vial. All in all, 2,937 vials were filled, which were then placed in a refrigerator for freezing at a temperature of −65° C. After freezing, the vials were transferred to a sublimator and the preparation was dried by lyophilization. Each vial contained 100 doses of the virus of titre $10^{3.45\quad 0.4}$ plaque-forming units per milliliter. The entire series contained 276,300 vaccine doses. Control tests gave favorable results, and the vaccine was distributed for actual use under a vaccination program.

EXAMPLE 2

"Vakchum" production in a cell subculture of green monkey kidney tissue previously stored in liquid nitrogen.

The methods of cell culture infection and virus cultivation duplicated the procedures described in detail in the previous example.

97 liters of a virus-containing fluid were harvested. After the fluid was poured into 100-ml vials, 33 ml per vial, and after the vaccine was lyophilized, 2,050 vials were obtained each containing 100 vaccine doses. The entire series consisted of 205,000 vaccine doses of titre $10^4$ plaque-forming units per milliliter. The vaccine successfully passed control tests and was distributed for preventive vaccination.

EXAMPLE 3

"Vackchum" manufacture in a continuous cell line of green monkey embryonal kidney tissue.

The continuous cell line culture was grown in 30 1.5-liter flasks. The continuous cell line was grown in the medium of Example 1 except that 10% calf serum was added to the medium.

The culture was infected with the Rokborn strain of the carnivore distemper virus preadapted to the primary cell culture of green monkey kidney tissue and the virus was grown in said culture in a medium with 0.5% lactalbuminhydrolysate in Earle's solution, pH 7.5, with 5 percent aminopeptide by weight at a temperature of 34° C. according to Example 1 to yield 16.7 liters of vaccine. All in all, 509 flasks were obtained, each containing 100 vaccine doses of titre $10^{3.98}$ plaque-forming units per ml. The whole series comprises 50900 vaccination doses. The vaccine was successfully tested and distributed for preventative vaccination.

EXAMPLE 4

Testing of "Vakchum" for safety for the mink and polar fox young.

The vaccine was employed in a dose of 1 ml of a preparation containing 3,000 plaque-forming units in 1 ml, which was prediluted in distilled water.

24 mink cubs and 12 polar fox cubs were vaccinated with "Vakchum", with 16 mink cubs and 3 polar fox cubs left unvaccinated as controls. Observations were conducted daily for 14 days. Throughout the entire experimental period all the animals remained clinically healthy.

EXAMPLE 5 a. Checking the "Vakchum" preparation for immunogenicity on polar fox cubs in a dose equal to that of Example 4.

3 polar foxes were vaccinated with "Vakchum". 50 days later these 3 foxes and 2 controls (unvaccinated against distemper) were infected with 1,500 lethal doses of the Gauyaskii strain. All 5 animals were observed daily. On the 15th day after the infection both controls were killed by distemper; the vaccinated foxes were subsequently observed for another week. Throughout the entire observation period (21 days after the infection) the vaccinated animals remained clinically healthy.

b. Checking the "Vakchum" preparation for immunogenicity on adult polar foxes using the dose of Example 4.

19 polar foxes received shots of "Vakchum". 21 days after the inoculation all the vaccinated animals and 6 controls (unvaccinated against distemper) were infected with the 1,000 lethal doses of Gauyaskii strain of the carnivore distemper virus. The observation period lasted for 21 days. On the 14th–16th day the controls (unvaccinated foxes) were killed by distemper, whereas all 19 vaccinated animals were in good health.

EXAMPLE 6

Checking the extent of immunization of mink cubs induced by "Vakchum" administered in the dose of Example 4.

In the course of summer vaccination, 5,333 Silver-Steelblu mink cubs were inoculated. In the period of vaccination and in the week that followed, all the animals were observed daily. All the vaccinated animals remained healthy.

EXAMPLE 7

Checking the length of immunity induced by "Vakchum" administered in the dose of Example 4 a. 6 polar foxes were vaccinated with the "Vakchum" preparation. 9 months after the vaccination, these 6 animals and 2 controls (unvaccinated foxes) were infected with 1,000 lethal doses of the highly pathogenic Gauyaskii strain of the carnivore distemper virus. 2 control foxes showed symptoms of distemper on the 10th and 11th day, respectively, and died, whereas the 6 foxes vaccinated against distemper showed no signs of the disease.

b. 3 polar foxes were vaccinated with "Vakchum" in the dose of Example 4. 27 months later these 3 animals and 6 controls (unvaccinated against distemper) were infected with 1,000 lethal doses of the Gauyaskii strain of carnivore distemper virus. All 6 controls developed distemper and died on the 12th–13th day, whereas the 3 foxes vaccinated with "Vakchum" 27 months previously remained unaffected.

EXAMPLE 8

Testing in a distemper focus.

At a fur farm with a high incidence of mink distemper a vaccination program was carried out using the "Vakchum" preparation administered in the dose of Example 4. First, 28 animals were vaccinated, putting an end to distemper in the group. Then another 12,170 minks were vaccinated, checking the morbidity entirely. Since then this farm has been free of distemper instances.

Large-scale field testing of the "Vakchum" preparation.

For 3 years, over 7,000,000 doses of "Vakchum" were used to vaccinate fur bearers (mink, polar fox, red fox and sable) at 36 farms located in different climatic zones.

The vaccination program demonstrated "Vakchum's" safety, high immunological and epizootological efficiency and also its economic advantages. Application of this preparation eradicated distemper at the farms which had earlier been known for a high incidence of this disease.

What we claim is;

1. A live virus culture vaccine useful against carnivore distemper and which is safe for animals, prepared by the sequential steps of (1) pre-adapting an attenuated strain of carnivore distemper virus to a cell culture of monkey (green monkey) kidney tissue by 8 to 10 passages at a temperature of 34(±0.2)C°, the incubation period for viral growth ranging from 4 to 5 days; (2) cultivating the adapted strain in the cell culture of monkey (green monkey) kidney tissue, which cell culture is selected from among a primary cell culture or a subculture, in the presence of a nutrient medium at a temperature of 34(±0.2)C°; (3) removing the resultant virus-containing fluid of the degenerated cell detritus of said culture; and (4) lyophilizing the liquid vaccine thus formed in the presence of a suitable virus thermostabilizer.

2. A method for preparing a live virus culture vaccine useful against carnivore distemper and which is safe for animals, which comprises the sequential steps of (1) pre-adapting an attenuated strain of carnivore distemper virus to a cell culture of monkey (green monkey) kidney tissue by 8 to 10 passages at a temperature of 34($\pm$0.2)C°, the incubation period for viral growth ranging from 4 to 5 days; (c) cultivating the adapted strain in the cell culture of monkey (green monkey) kidney tissue, which cell culture is selected from among a primary cell culture or a subculture, in the presence of a nutrient medium at a temperature of 34($\pm$0.2)C°; (3) removing the resultant virus-containing fluid of the degenerated cell detritus of said culture; and (4) lyophilizing the liquid vaccine thus formed in the presence of a suitable virus thermostabilizer.

3. The method of claim 2, wherein the cultivation of the carnivore distemper virus is carried out in a cell culture of monkey (green monkey) kidney tissue reconstituted following storage in liquid nitrogen.

4. The method of claim 2, wherein, in order to increase the yield of the carnivore distemper virus and to achieve a more complete use of the cell culture in cultivating the strain, at least a 3-fold replacement of the virus-containing fluid is carried out by a fresh nutrient medium to the point of total cell degradation of said culture.

5. The method of claim 4, wherein the virus-containing fluid is removed for the first time after approximately 30 to 40% of the cells of said culture exhibit a cytopathic effect.

6. The method of claim 2, wherein the virus-containing fluid is lyophilized in the presence of 4.5 to 5.5% sorbite by weight and 1.4 to 1.6% gelatose by weight, said sorbite and said gelatose serving as thermostabilizers.

* * * * *